United States Patent [19]

Ballard et al.

[11] Patent Number: 5,164,370

[45] Date of Patent: Nov. 17, 1992

[54] PEPTIDE ANALOGUES OF INSULIN-LIKE GROWTH FACTOR 1 (IGF-1) OR FACTOR 2 (IGF-2)

[75] Inventors: Francis J. Ballard, Glenalta; John C. Wallace, Coromandel Valley; Julian R. E. Wells, College Park, all of Australia

[73] Assignee: Gropep Pty. Ltd., Adelaide, Australia

[21] Appl. No.: 408,518

[22] PCT Filed: Dec. 20, 1988

[86] PCT No.: PCT/AU88/00485

§ 371 Date: Aug. 24, 1989

§ 102(e) Date: Aug. 24, 1989

[87] PCT Pub. No.: WO89/05822

PCT Pub. Date: Jun. 29, 1989

[30] Foreign Application Priority Data

Dec. 24, 1987 [AU] Australia .................. PI6068

[51] Int. Cl.⁵ .................. A61K 37/02; C07K 5/00
[52] U.S. Cl. .................. 514/12; 530/324; 930/120
[58] Field of Search .................. 514/2, 12, 3, 4; 530/330, 331, 303, 324; 930/120

[56] References Cited

U.S. PATENT DOCUMENTS 408,518 10/1889 Applebaum et al. .................. 514/3
4,876,242 10/1989 Applebaum et al. .

FOREIGN PATENT DOCUMENTS 0158892 10/1985 European Pat. Off. .
0227619 1/1987 European Pat. Off. .
0309050 3/1989 European Pat. Off. .
0379338 7/1990 European Pat. Off. .
8600246 of 1987 PCT Int'l Appl. .
WO8701038 2/1987 PCT Int'l Appl. .
WO8500831 of 1985 World Int. Prop. O. .

OTHER PUBLICATIONS

Rudinger, Pept. de Hormones, Parsons (Ed) U. Park Press, Baltimore (1976).
Merritielo, Agen Chem Int Ed 24 (1985) 799–810.
CA 108: 202006r (1988) Dawe et al.
CA 109: 86924h (1988) Cascieri et al.
CA 104: 203501c (1986).
Rudinger, *Peptide Hormones* (Parsons, Ed. 1976) 1–5.
*Chemical Abstracts*, vol. 108, No. 23, Abs. No. 198502e (1988) Francis et al.
*Chemical Abstracts*, vol. 109, No. 3, Abs. No. 17150r (1988) Bayne et al.
*Chemical Abstracts*, vol. 105, No. 5, Abs. No. 36363w (1986) Carlsson-Skwirut et al.
*Chemical Abstracts*, vol. 105, No. 9, Abs. No. 73328j (1986) Sara et al.
*Chemical Abstracts*, vol. 106, No. 13, Abs. No. 96902b (1987) Carlsson-Skwirut et al.
Sara et al., *Proc. Nat'l Acad., USA*, 83, 4900–4907 (1986).
Carlsson-Skwirut et al., *FEBS*, 201, No. 1, 46–50 (1986).
*Chemical Abstracts*, vol. 104, No. 23, Abs. No. 203501c (1986) Blumberg et al.
*Chemical Abstracts*, vol. 97, No. 3, Abs. No. 24215c (1982) Nokihara et al.
Fagerstedt et al., *ACTA Endoctrinol*, 103, (256), 216 (1983).
The Merck Index, 10th ed., No. 8560, 4354, 7685, 4330, 9229 and 5288 at pp. 1246, 645, 1121, 641, 1344 and 782, respectively (1983).
Svoboda et al., *Biochemistry*, 19, 790–797 (1980).
Sara et al., *Proc. Nat'l Acad. Sci., USA*, 78, 3175–3179 (1981).
M. Ross et al., *Biochem. J.*, 258, 267–272 (1989).
C. J. Bagley et al., *Biochem. J.*, 259, 665–671 (1989).
M. M. J. Giacobini et al., is believed to have been published in *Science* in either 1989 or 1990.
E. Rindernecht et al., *J. Biol. Chem.*, 253, 2769–2776 (1978).
F. J. Ballard et al., *Biochem. and Biophys. Res. Commun.*, 149, 398–404 (1987).
C. Carlsson-Skwirut et al., *Biochim. Biophys. Acta*, 1011, 192–197 (1989).

Primary Examiner—Merrell C. Cashion, Jr.
Assistant Examiner—B. Celsa
Attorney, Agent, or Firm—Merchant, Gould, Smith, Edell, Welter & Schmidt

[57] ABSTRACT

Peptide analogues of insulin-like growth factor 1 and growth factor 2 are disclosed. When the analogue is an analogue of growth factor 1 the glutamic acid residue is absent from position 3 of the N-terminal and either the glutamic acid residue or the threonine residue adjacent to glutamic acid residue at position 3 is replaced by a different amino acid residue. When the peptide analogue is an analogue of insulin growth factor 2 the glutamic acid residue position 5 is absent. Preferred peptide analogues are disclosed. Methods of use in pharmaceutical and veterinary preparations are described.

8 Claims, No Drawings

PEPTIDE ANALOGUES OF INSULIN-LIKE GROWTH FACTOR 1 (IGF-1) OR FACTOR 2 (IGF-2)

This invention relates to growth factors, related compounds and their use.

Insulin-like growth factor-1, a somatomedin, is a small protein that has been shown to stimulate growth of a wide range of cells in culture. Human IGF-1 (hIGF-1) has been purified to homogeneity from human serum and its complete amino acid sequence established. The serum mediator of growth hormone action, somatomedin C, has been shown to have an identical sequence to hIGF-1 so that these two are now considered as being synonymous. The amino acid sequence established for hIGF-1 beginning with the N-terminal glycine is:

Gly-pro-glu-thr-leu-cys-gly-ala-glu-leu-val-asp-ala-leu-gin-phe-val-cys-gly-asp-arg-gly-phe-tyr-phe-asn-lys-pro-thr-gly-tyr-gly-ser-ser-ser-arg-arg-ala-pro-gin-thr-gly-ile-val-asp-glu-cys-cys-phe-arg-ser-cys-asp-leu-arg-arg-leu-glu-met-tyr-cys-ala-pro-leu-lys-pro-ala-lys-ser-ala- Bovine IGF-1 and porcine IGF-1 have identical sequences.

Using the conventional numbering system of the N-terminal glycine being residue #1 and the C-terminal alanine residue #70, ovine and chicken IGF-1 differ from human IGF-1 only as follows:
ovine IGF-1: ala[66]
Chicken IGF-1: ser[26]; lys[41]; gln[50]; ile[64]

IGF-1 levels in serum correlate positively with growth rates in boys during adolescence and negatively with the degree of growth hormone deficiency in growth-retarded subjects, and to both growth rate and eventual size in mice transfected with growth hormone genes. These findings, indirectly linking IGF-1 concentrations with growth rates and supported by more direct evidence that administration of IGF-1 leads to restoration of growth rates in hypopituitary (growth hormone deficient) rats or mice and to increased growth rates in normal rats, have lead to the interpretation that IGF-1 might usefully be applied: (1) in humans to treat growth hormone deficiencies; (2) in farm animals to increase growth rates, increase the relative proportion of muscle and enhance food conversion efficiency. It is further suggested that administration of IGF-1: (3) may suppress the loss of body protein in severe human catabolic states such as following burns, infection or other trauma; (4) may improve wound healing in human subjects as well as in animals. IGF-1 can also be used to (5) support the growth of cells in culture.

The result of the above inferences is that there is a commercial demand for IGF-1 for use in animal trials, clinical investigations and for cell culture. However, only milligram amounts of hIGF-1, for example, are available by purification of tonnes of human serum protein and yields from recombinant DNA methods remain low.

Insulin-like growth factor-2 (IGF-2) like IGF-1, is a small protein that has been shown to stimulate growth of cells in culture. In most cases, these biological effects occur following interaction of IGF-2 with the same cellular receptor as is involved in IGF-1 actions. The amino acid sequence established for human IGF-2 (hIGF-2) beginning with the N-terminal alanine is shown below. Upper case letters have been used to indicate the amino acids equivalent to the N-terminal 5 amino acids of hIGF-1:

Ala-tyr-arg-PRO-SER-GLU-THR-LEU-cys-gly-gly-glu-leu-val-asp-thr-leu-gln-phe-val-cys-gly-asp-arg-gly-phe-tyr-phe-ser-arg-pro-ala-ser-arg-val-ser-arg-arg-ser-arg-gly-ile-val-glu-glu-cys-cys-phe-arg-ser-cys-asp-leu-ala-leu-leu-glu-thr-tyr-cys-ala-thr-pro-ala-lys-ser-glu Using the conventional numbering system of the N-terminal alanine being residue #1 and the C-terminal glutamic acid being residue #67, bovine, ovine, porcine and chicken IGF-2 differ from human IGF-2 only as follows:
bovine IGF-2: ser[32]; ile[35]; asn[36]
ovine IGF-2: ser[32]; ile[35]; asn[36]; ala[62]
porcine IGF-2: asn[36]
chicken IGF-2: ala[1] missing; gly[3]; thr4; ala[5]; val[32]; gly[33]; asn[35]; asn[36]; ile[39]; asn[40]

It has been disclosed (see PCT/AU87/00246 to applicants) that compounds corresponding to IGF-1 but lacking one to five, preferably three amino acid residues from the N-terminal cf the molecule can exhibit a substantial increase in biological potency compared with the more complete compounds.

For example, the compound destripeptide bIGF-1 but lacking the amino acid residues gly, pro and glu from the N-terminal, is effective in inhibiting protein breakdown and stimulating both protein synthesis and DNA synthesis in cellular systems at concentrations between 4 and 50 fold lower than required for entire bIGF-1.

For IGF-1 peptides having N-terminal amino acid sequences in common with that of human/bovine/porcine IGF-1, the elimination of between 1 and 5 amino acid residues from the N-terminal also results in enchanced biological potencies. The said N-terminal amino acid sequence is also a feature of the IGF-1 of rat, ovine, and chicken species.

However, a useful property of the full IGF-1 peptide but not shared by the IGF-1 peptides having 1 to 5 N-terminal amino acids eliminated is that production by recombinant DNA methods that are part of the prior art are facilitated by the existence of N-terminal glycine. This facilitation occurs because an asparagine residue can be engineered upstream from the glycine and the asparagine/glycine bond cleaved selectively by mild hydroxylamine treatment following expression of the engineered gene.

Accordingly it is an object of the present invention to overcome, or at least alleviate, one or more of the difficulties related to the prior art.

Accordingly in a first aspect of the present invention there is provided a peptide analogue of insulin-like growth factor-1 (IGF-1) or factor-2 (IGF-2) wherein at least the glutamic acid residue is absent at position 3 from the N-terminal of IGF-1 or at position 5 or 6 from the N-terminal of IGF-2. It will be understood that in respect of chicken IGF-2 the N-terminal Ala-residue is absent so that the glutamic acid residue is at position 5 from the N-terminal.

Preferably the peptide analogue is a human, bovine, ovine, porcine or chicken insulin-like growth factor analogue. More preferably the peptide analogue is a human, bovine or porcine insulin-like growth factor-1 analogue.

The peptide analogue according to the present invention may be in a biologically pure form.

In a preferred aspect of the present invention, wherein the peptide analogue, is an insulin like growth factor-1 analogue in addition at least one of the Gly-, Pro-, or Thr- residues may be absent from the N-terminal in addition to the absence of the glutamic acid residue.

In a preferred aspect of the present invention the glutamic acid residue may be replaced by a different amino acid residue.

Suitable amino acid residues to replace glutamic acid include glycine, glutamine, leucine, arginine, or lysine.

More preferably the replacement residue for glutamic acid will be a positively charged amino acid residue such as arginine or lysine. Alternatively the glutamic acid residue may be replaced by glycine and the threonine residue normally adjacent to the glutamic acid may be replaced by a different amino acid residue, preferably arginine or glycine, most preferably arginine. Preferably the N-terminal sequence is selected from

| |
|---|
| Val—Leu—Cys— |
| Arg—Leu—Cys— |
| Gly—Leu—Cys— |
| Gly—Thr—Leu—Cys— |
| Gly—Pro—Arg—Thr—Leu—Cys— |
| Gly—Pro—Gly—Arg—Leu—Cys— |
| Gly—Pro—Gly—Gly—Leu—Cys— |
| Gly—Pro—Gly—Thr—Leu—Cys— |
| Gly—Pro—Gln—Thr—Leu—Cys— |
| Gly—Pro—Lys—Thr—Leu—Cys— |
| Gly—Pro—Leu—Thr—Leu—Cys— | with the Cys residue shown being that normally at position 6 from the N-terminal.

In a further preferred aspect of the present invention the peptide analogue is an insulin-like growth factor-2 analogue. Preferably in the peptide analogue, at least one of the Ala-, Tyr-, Arg-, Pro-, Ser- or Thr- residues is absent from the N-terminal in addition to the absence of the glutamic acid residue.

More preferably the glutamic acid residue is replaced by a different amino acid residue.

Suitable amino acid residues to replace glutamic acid include glycine, glutamine, leucine, arginine, or lysine. Suitable amino acid residues to replace the threonine residue include arginine or glycine.

More preferably the replacement residue for glutamic acid will be a positively charged amino acid residue such as arginine or lysine. Alternatively the glutamic acid residue may be replaced by glycine and the threonine residue normally adjacent to the glutamic acid may be replaced by a different amino acid residue, preferably arginine or glycine, most preferably arginine. Preferably the N-terminal sequence is selected from Ala-Tyr-Arg-Pro-Ser-Lys-Thr-Leu-Cys-Ala-Tyr-Arg-Pro-Ser-Arg-Thr-Leu-Cys-Ala-Tyr-Arg-Pro-Ser-Gly-Arg-Leu-Cys-Ala-Tyr-Arg-Pro-Ser-Gly-Thr-Leu-Cyswith the Cys residue shown being that normally at position 9 from the N-terminal.

The peptides lacking the glutamic acid residue bind poorly to the binding proteins produced by many cell types. This binding may be further reduced by the substitution of an arginine or lysine residue for the glutamic acid residue and optionally the substitution of the adjacent threonine residue by arginine or a lysine residue. Should a binding protein be present those other IGF-1 peptides that do bind have reduced potencies.

In a preferred aspect wherein the glutamic acid residue is either substituted by another amino acid or eliminated and the N-terminal residue is glycine, this invention provides peptide analogues that are suitable for cleavage of an engineered upstream asparagine. The peptide analogues have higher potencies than IGF-1 in cultured cells.

The peptide analogues according to the present invention may form suitable replacements for IGF-1 and -2 in the following applications: (1) in humans to treat growth hormone deficiencies; (2) in farm animals to increase growth rates, increase the relative proportion of muscle or improve food conversion efficiency; (3) in humans to suppress the loss of body protein in severe catabolic states such as following burns, infection or other trauma; (4) in humans and animals to improve wound healing, and (5) to support the growth of cells in culture:

More specifically, the present invention provides a pharmaceutical or veterinary composition that includes:

(a) an effective amount of a peptide analogue of insulin like growth factor-1 (IGF-1) or factor-2 (IGF-2) wherein at least the glutamic acid residue is absent at position 3 from the N-terminal of IGF-1 or at position 6 from the N-terminal of IGF-2 respectively and (b) a pharmaceutically or veterinarily acceptable diluent, carrier or excipient therefor.

The peptide analogue may be present in amounts sufficient to provide a dose rate of approximately 0.01 to 10, preferably 0.1 to 1 milligrams/kg body weight/day. The peptide analogue may be present in amounts of from approximately 0.02 to 2000 milligrams. For cell culture applications the peptide analogue may be present in concentrations from approximately 0.1 to 100 milligrams per litre.

In a further preferred aspect of the present invention there is provided a method for the treatment of protein accumulation deficiencies or protein loss in human subjects, which method includes administering to a patient to be treated an effective amount of a peptide analogue of insulin-like growth factor-1 (IGF-1) or factor-2 (IGF-2) wherein at least the glutamic acid residue is absent at position 3 from the N-terminal of IGF-1 or at position 6 from the N-terminal of IGF-2 respectively.

The peptide analogues may be administered to human subjects as a treatment for disorders associated with tissue wasting including, but not limited to, burns, skeletal trauma, infection, cancer, cystic fibrosis, Duchenne muscular dystrophy, Becker dystrophy, autosomal recessive dystrophy, polymyositis as well as other myopathies and acquired immune deficiency syndrome (AIDS). The peptide analogues may be administered parenterally or by injection.

In an alternative aspect there is provided a method for the treatment of wounds in animals including humans, which method includes administering to a patient to be treated an effective amount of a peptide analogue of mammalian insulin-like growth factor-1 (IGF-1) or factor-2 (IGF-2) wherein at least the glutamic acid residue is absent at position 3 from the N-terminal of IGF-1 or at position 6 from the N-terminal of IGF-2 respectively.

For the treatment of wounds in human subjects or in animals the peptide analogue may be applied externally to the wound or it may be administered by injection.

In a still further aspect there is provided a method for the improvement of growth performance in animals which method includes administering to an animal to be treated an effective amount of a peptide analogue of insulin-like growth factor-1 (IGF-1) or factor-2 (IGF-2) wherein at least the glutamic acid residue is absent at position 3 from the N-terminal of IGF-1 or at position 6 from the N-terminal of IGF-2 respectively.

An implant, preferably a slow release pellet, is the preferred method of administration to farm animals as applied in conventional practice. Otherwise the peptide analogue may be administered by injection.

The peptide analogues of the present invention may be administered to premature or other human infants to promote growth, improve nitrogen status and to treat catabolic disorders. The peptides may be administered as outlined above for tissue wasting conditions.

Accordingly in a still further aspect of the present invention, there is provided a method for the stimulation of cells in culture which method includes providing
a culture medium, and
an effective amount of a peptide analogue as described above; and
adding the peptide analogue to the culture medium.

Any standard culture medium may be used in accordance with this aspect of the present invention. For example the culture medium may include Eagle's Minimal Essential Medium.

In a further aspect of the present invention there is provided a method for the preparation of a peptide analogue of IGF-1 wherein at least the glutamic acid residue is absent at position 3 from the N-terminal which method includes
providing a source of amino acids, and
coupling the amino acids in sequence to form a peptide analogue having an N-terminal sequence selected from,

| |
|---|
| Val—Leu—Cys— |
| Arg—Leu—Cys— |
| Gly—Leu—Cys— |
| Gly—Thr—Leu—Cys— |
| Gly—Pro—Arg—Thr—Leu—Cys— |
| Gly—Pro—Gly—Arg—Leu—Cys— |
| Gly—Pro—Gly—Gly—Leu—Cys— |
| Gly—Pro—Gly—Thr—Leu—Cys— |
| Gly—Pro—Gln—Thr—Leu—Cys— |
| Gly—Pro—Lys—Thr—Leu—Cys— |
| Gly—Pro—Leu—Thr—Leu—Cys— | with the Cys residue being that normally at position 6 from the N-terminal.

The peptide analogues may be produced by appropriate modifications to methods existing for the production of the full IGF-1 peptide. these modifications would be familiar to those familiar with the art.

Specifically, the peptides related to human/bovine/porcine IGF-1 may be synthesised chemically using procedures developed for human IGF-1 (for example: Li et al., Proc. Natl. Acad. Sci, USA 80: 2216–2220, 1983) but with the final cycles of amino acid ligation modified. Synthetic ovine or chicken IGF-1 as well as related IGF-1 and IGF-2 peptides may be produced by techniques similar to those used for human IGF-1 using amino acid sequence information for these peptides.

In accordance with the present invention, the peptides may also be produced following transformation of susceptible bacterial, yeast or tissue culture cell hosts with recombinant plasmids that include DNA sequences capable of directing the expression of the peptides. The DNA sequence may be synthetic, chromosomal, cDNA or combination thereof. The inserted coding sequences may incorporate deletion or omissions to account for differences between the sequence of Peptide analogues and the full IGF-1 peptide.

The present invention will now be more fully described with respect to production of certain IGF-1 peptides and information on their biological potencies. It should be understood however, that the following description is illustrative only and should not be taken in any way as a restriction on the generality of the description foregoing.

EXAMPLE 1

Synthesis of IGF-1 peptides

Chemical synthesis of human/bovine/porcine IGF-1 peptides with between 1 and 4 amino acids from the normal N-terminal modified has been effected by the following procedure.

The starting material was Boc-ala-phenylacetamido methyl resin. Coupling was effected in an Applied Biosystems Inc model 430A peptide synthesiser with preformed symmetric anhydrides of the Boc-aminoacids in dichloromethane except for the derivatives of arginine, asparagine and glutamine which were coupled in dimethyl formamide (DMF). In all cases a second coupling was performed in DMF. Samples of resin were removed after each cycle of synthesis and subjected to quantitive ninhydrin analysis (Sarin, V. K., Kent, S. B. H., Tam, J. P., Merifield, R. B.; Anal. Biochem. 17, 147–157 (1981). Preview sequence analysis of the side-chain protected, resin-bound peptide was also carried out and together, these indicated an average repetitive yield of 99%.

Portions of resin containing side-chain protected peptides corresponding to the complete sequence of hIGF-1 but with 4 to 0 amino acids not coupled at the N-terminal were removed. Other portions with between 4 and 3 amino acids not coupled at the N-terminal had amino acid residues coupled as required for specific analogues. Peptides were cleaved and deprotected according to Applied Biosystems Inc procedures and recovered as ether precipitates.

Peptides were redissolved in 6M guanidine hydrochloride pH 8.5 with Tris containing 10 mM dithioerythritol and desalted by reverse phase HPLC and dried. Oxidation of the reduced peptide was effected by dissolving in 8M urea, 0.1M Tris (pH8.0 with HCl) containing 13 mM oxidized gluthathione and incubated at 25° for 15 hours. The sample was purified by reverse phase HPLC using a gradient of acetonitrile in 0.1% trifluoroacetic acid to elute the peptides and separate the biologically active form of the peptide from those forms lacking the correct disulphide bonds and hence lacking full biological activity. The samples were dried prior to resuspension.

Biological activity was confirmed by the ability of the peptide to stimulate protein synthesis in L6 myoblasts.

It will be appreciated that various modifications and/or alterations may be introduced into the constructions and arrangements of parts previously described without departing from the spirit or ambit of the present invention.

Biological Activities of IGF-1 Peptides

Bioassays of purified synthetic peptides have been compared with pure human/bovine/porcine IGF-1. The assays involve the incorporation of 3H-labelled leucine into the total cell protein of L6 myoblasts as described by Francis et al. (Biochem. J. 233:207-213, 1986). The relative potencies are shown in Table 1 where the concentrations are expressed as percentages of that required to give a half-response with human/bovine/porcine IGF-1 (12 ng/ml):

TABLE 1

Relative biological potencies of IGF-1 peptides in L6 myoblasts

| N-terminal sequence (the Cys residue is that normally at position 6 from the N-terminal) Human/bovine/porcine IGF-1 | Concentration (percent of that required to give a half-response with hIGF-1) |
|---|---|
| (Gly—Pro—Glu—Thr—Leu—Cys—) | 100 |
| Thr—Leu—Cys— | 15 |
| Val—Leu—Cys— | 13 |
| Gly—Leu—Cys— | 15 |
| Arg—Leu—Cys— | 4 |
| Gly—Thr—Leu—Cys— | 16 |
| Gly—Pro—Gly—Thr—Leu—Cys— | 12 |
| Gly—Pro—Gln—Thr—Leu—Cys— | 18 |
| Gly—Pro—Lys—Thr—Leu—Cys— | 11 |
| Gly—Pro—Leu—Thr—Leu—Cys— | 18 |
| Gly—Pro—Arg—Thr—Leu—Cys— | 5 |
| Gly—Pro—Gly—Gly—Leu—Cys— | 14 |
| Gly—Pro—Gly—Arg—Leu—Cys— | 4 |

The higher potencies produced by the deletion or modification of the glutamic acid residue normally at position 3 of IGF-1 are not associated with a markedly increased competition of the peptide for binding to receptors on the L6 myoblasts, provided that binding is carried out at 4° C. otherwise using the method of Ballard et al (Biochem. J. 233; 223-230, 1986) with human/bovine/porcine IGF-1 as radioligand. This apparent discrepancy is caused by the myoblasts producing a binding protein in addition to the receptor. This binding protein selectively binds those IGF-1 peptides that have a glutamic acid residue at position 3 from the N-terminal, thus preventing the peptide binding to the cell receptor. This interpretation is established by the following results [determined by the method of Martin and Baxter, J. Biol, Chem. 261: 8754-8760, (1986)] with purified binding proteins (see Table 2).

TABLE 2

Relative abilities of IGF-1 Peptides to complete for the binding of labelled human/bovine/porcine IGF-1 to purified binding protein

| N-terminal sequence (the Cys residue is that normally at position 6 from the N-terminal) Human/bovine IGF-1 | Potency for binding to the protein where hIGF-1 = 100% |
|---|---|
| (Gly—Pro—Glu—Thr—Leu—Cys—) | 100 |
| Thr—Leu—Cys— | 0.2 |
| Val—Leu—Cys— | 0.1 |
| Gly—Leu—Cys— | 0.1 |
| Arg—Leu—Cys— | <0.1 |
| Gly—Thr—Leu—Cys— | 1.0 |
| Gly—Pro—Gly—Thr—Leu—Cys— | 0.5 |
| Gly—Pro—Gln—Thr—Leu—Cys— | 1.0 |
| Gly—Pro—Lys—Thr—Leu—Cys— | 0.1 |
| Gly—Pro—Leu—Thr—Leu—Cys— | 0.5 |
| Gly—Pro—Arg—Thr—Leu—Cys— | <0.1 |
| Gly—Pro—Gly—Gly—Leu—Cys— | 0.1 |
| Gly—Pro—Gly—Arg—Leu—Cys— | <0.1 |

Accordingly, from the data presented in Tables 1 and 2 it can be seen that:

removal of the three N-terminal amino acids (Gly,Pro,Glu) from hIGF-1 leads to enhanced biological activity and minimal binding to binding proteins produced by the cells;

removal of the three N-terminal amino acids together with substitution of the fourth amino acid (threonine) with arginine gives even greater biological potency as well as even lower binding to the binding proteins;

removal of the two N-terminal amino acids (Gly,Pro) together with the substitution of the third amino acid (glutamic acid) with glycine leads to an IGF analogue that is more active biologically than hIGF-1 and binds poorly but significantly to the binding proteins;

substitution of the Glutamic acid residue normally at position 3 in hIGF-1 with glycine, glutamine, lysine, leucine or arginine leads to enhanced potency and poor binding to binding proteins, with the effects greatest with the lysine or arginine substitutions;

substitution of the glutamic acid residue normally at position 3 in hIGF-1 with glycine together with substitutions of glycine, arginine or valine for threonine at position 4 also produce increases in potency and decreased binding to binding proteins.

Finally, it is to be understood that various other modifications and/or alterations may be made without departing from the spirit of the present invention as outlined herein.

We claim:

1. A peptide analogue of insulin growth factor-1 (IGF-1) having a modified N-terminal sequence selected from:

Val—Leu—Cys—

Arg—Leu—Cys—

Gly—Leu—Cys—

Gly—Pro—Arg—Thr—Leu—Cys—

Gly—Pro—Gly—Arg—Leu—Cys—

Gly—Pro—Gly—Gly—Leu—Cys—

Gly—Pro—Gly—Thr—Leu—Cys—

Gly—Pro—Lys—Thr—Leu—Cys—

Gly—Pro—Leu—Thr—Leu—Cys— with the Cys residue shown being that normally at position 6 from the N-terminal, the remainder of the sequence corresponding to a human, bovine, ovine, porcine or chicken insulin growth factor-1.

2. A peptide analogue according to claim 1 which is human, bovine or porcine insulin growth factor-1 analogue.

3. A peptide analogue according to claim 2 in a biologically pure form.

4. A peptide analogue of insulin growth factor-2 (IGF-2) having a modified N-terminal sequence selected from:
Ala-Thr-Arg-Pro-Ser-Lys-Thr-Leu-Cys-Ala-Tyr-Arg-Pro-Ser-Arg-Thr-Leu-Cys-Ala-Tyr-Arg-Pro-Ser-Gly-Arg-Leu-Cys-Ala-Tyr-Arg-Pro-Ser-Gly-Arg-Leu-Cyswith the Cys residue shown being that normally at position 9 from the N-terminal, the remainder of the sequence corresponding to a human, bovine, ovine, porcine or chicken insulin growth factor-2.

5. A peptide analogue according to claim 4 which is human, bovine, or porcine insulin growth factor-2 analogue.

6. A peptide analogue according to claim 5 in a biologically pure form.

7. A pharmaceutical or veterinary composition for the treatment of protein loss in humans or animals respectively, including an effective amount of a peptide analogue of insulin growth factor-1 (IGF-1) having a modified N-terminal sequence selected from:

Val—Leu—Cys—

Arg—Leu—Cys—

Gly—Leu—Cys—

Gly—Pro—Arg—Thr—Leu—Cys—

Gly—Pro—Gly—Arg—Leu—Cys—

Gly—Pro—Gly—Gly—Leu—Cys—

Gly—Pro—Gly—Thr—Leu—Cys—

Gly—Pro—Lys—Thr—Leu—Cys—

Gly—Pro—Leu—Thr—Leu—Cys— with the Cys residue shown being that normally at position 6 from the N-terminal, the remainder of the sequence corresponding to a human, bovine, ovine, porcine or chicken insulin growth factor-1.

8. A pharmaceutical or veterinary composition for the treatment of protein loss in humans or animals respectively, including an effective amount of a peptide analogue of insulin growth factor-2 (IGF-2) having a modified N-terminal sequence selected from:
Ala-Thr-Arg-Pro-Ser-Lys-Thr-Leu-Cys-Ala-Tyr-Arg-Pro-Ser-Arg-Thr-Leu-Cys-Ala-Tyr-Arg-Pro-Ser-Gly-Arg-Leu-Cys-Ala-Tyr-Arg-Pro-Ser-Gly-Thr-Leu-Cyswith the Cys residue shown being that normally at position 9 from the N-terminal, the remainder of the sequence corresponding to a human, bovine, ovine, porcine or chicken insulin growth factor-2.

* * * * *

UNITED STATES PATENT AND TRADEMARK OFFICE
CERTIFICATE OF CORRECTION

PATENT NO. : 5,164,370

DATED : November 17, 1994

INVENTOR(S) : Ballard et al.

Page 1 of 2

It is certified that error appears in the above-indentified patent and that said Letters Patent is hereby corrected as shown below:

In Claim 4, at col 8, lines 63-66, delete the sequence "Ala-Thr-Arg-Pro-Ser-Lys-Thr-Leu-Cys-Ala-Tyr-Arg-Pro-Ser-Arg-Thr-Leu-Cys-Ala-Tyr-Arg-Pro-Ser-Gly-Arg-Leu-Cys-Ala-Tyr-Arg-Pro-Ser-Gly-Arg-Leu-Cys" and insert in its place the four sequences -- Ala-Thr-Arg-Pro-Ser-Lys-Thr-Leu-Cys-
Ala-Tyr-Arg-Pro-Ser-Arg-Thr-Leu-Cys-
Ala-Tyr-Arg-Pro-Ser-Gly-Arg-Leu-Cys-
Ala-Tyr-Arg-Pro-Ser-Gly-Arg-Leu-Cys- --.

UNITED STATES PATENT AND TRADEMARK OFFICE
CERTIFICATE OF CORRECTION

PATENT NO. : 5,164,370
DATED : November 17, 1994
INVENTOR(S) : Ballard et al.

It is certified that error appears in the above-indentified patent and that said Letters Patent is hereby corrected as shown below:

In Claim 8, at col 10, lines 17-20, delete the sequence "Ala-Thr-Arg-Pro-Ser-Lys-Thr-Leu-Cys-Ala-Tyr-Arg-Pro-Ser-Arg-Thr-Leu-Cys-Ala-Tyr-Arg-Pro-Ser-Gly-Arg-Leu-Cys-Ala-Tyr-Arg-Pro-Ser-Gly-Arg-Leu-Cys" and insert in its place the four sequences -- Ala-Thr-Arg-Pro-Ser-Lys-Thr-Leu-Cys-
   Ala-Tyr-Arg-Pro-Ser-Arg-Thr-Leu-Cys-
   Ala-Tyr-Arg-Pro-Ser-Gly-Arg-Leu-Cys-
   Ala-Tyr-Arg-Pro-Ser-Gly-Arg-Leu-Cys- --.

Signed and Sealed this

Twenty-first Day of March, 1995

Attest:

BRUCE LEHMAN

Attesting Officer      Commissioner of Patents and Trademarks

UNITED STATES PATENT AND TRADEMARK OFFICE
CERTIFICATE OF CORRECTION

PATENT NO. : 5,164,370

DATED : November 17, 1992

INVENTOR(S) : Ballard et al.

It is certified that error appears in the above-identified patent and that said Letters Patent is hereby corrected as shown below:

In Claim 4, at col 8, lines 63-66, delete the sequence "Ala-Thr-Arg-Pro-Ser-Lys-Thr-Leu-Cys-Ala-Tyr-Arg-Pro-Ser-Arg-Thr-Leu-Cys-Ala-Tyr-Arg-Pro-Ser-Gly-Arg-Leu-Cys-Ala-Tyr-Arg-Pro-Ser-Gly-Arg-Leu-Cys" and insert in its place the four sequences -- Ala-Tyr-Arg-Pro-Ser-Lys-Thr-Leu-Cys-
Ala-Tyr-Arg-Pro-Ser-Arg-Thr-Leu-Cys-
Ala-Tyr-Arg-Pro-Ser-Gly-Arg-Leu-Cys-
Ala-Tyr-Arg-Pro-Ser-Gly-Thr-Leu-Cys- --.

In Claim 8, at col 10, lines 17-20, delete the sequence "Ala-Thr-Arg-Pro-Ser-Lys-Thr-Leu-Cys-Ala-Tyr-Arg-Pro-Ser-Arg-Thr-Leu-Cys-Ala-Tyr-Arg-Pro-Ser-Gly-Arg-Leu-Cys-Ala-Tyr-Arg-Pro-Ser-Gly-Arg-Leu-Cys" and insert in its place the four sequences -- Ala-Tyr-Arg-Pro-Ser-Lys-Thr-Leu-Cys-
Ala-Tyr-Arg-Pro-Ser-Arg-Thr-Leu-Cys-
Ala-Tyr-Arg-Pro-Ser-Gly-Arg-Leu-Cys-
Ala-Tyr-Arg-Pro-Ser-Gly-Thr-Leu-Cys- --.

Signed and Sealed this

Eighth Day of August, 1995

*Attest:*

BRUCE LEHMAN

*Attesting Officer*    *Commissioner of Patents and Trademarks*

UNITED STATES PATENT AND TRADEMARK OFFICE
Certificate

Patent No. 5,164,370                  Patented: November 17, 1992

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Francis J. Ballard, Glenalta, Australia; John C. Wallace, Coromandel Valley, Australia; Julian R. E. Wells (deceased), College Park, Australia; Christopher Bagley, Fullarton, South Australia; and Geoffrey L. Francis, Athelstone, South Australia.

Signed and Sealed this Third Day of April 2007.

<div style="text-align:right">

WILLIAM R. DIXON, JR.
*Special Program Examiner*
Technology Center 1600

</div>